United States Patent
Robinson et al.

(10) Patent No.: US 10,228,351 B2
(45) Date of Patent: Mar. 12, 2019

(54) ACOUSTIC DETECTION IN PROCESS ENVIRONMENTS

(71) Applicant: Rosemount Inc., Chanhassen, MN (US)

(72) Inventors: Cory Michael Robinson, Mayer, MN (US); Marcos Antonio Vieira Peluso, Chanhassen, MN (US); Theodore Henry Schnaare, Carver, MN (US); Ryan Thomas Lindsey, Eden Prairie, MN (US); Lynn LeRoy Faulkner, Westerville, OH (US)

(73) Assignee: ROSEMOUNT INC., Chanhassen, MN (US)

( * ) Notice: Subject to any disclaimer, the term of this patent is extended or adjusted under 35 U.S.C. 154(b) by 402 days.

(21) Appl. No.: 14/494,865

(22) Filed: Sep. 24, 2014

(65) Prior Publication Data

US 2016/0084801 A1 Mar. 24, 2016

(51) Int. Cl.
*G01N 29/11* (2006.01)
*G10K 11/178* (2006.01)
(Continued)

(52) U.S. Cl.
CPC ............ *G01N 29/11* (2013.01); *G01N 29/14* (2013.01); *G01N 29/32* (2013.01);
(Continued)

(58) Field of Classification Search
CPC .. G01N 29/14; G01N 29/4463; G01N 29/223; G01N 29/227; G01N 29/228;
(Continued)

(56) References Cited

U.S. PATENT DOCUMENTS

| 4,640,121 A | * | 2/1987 | Leuker .................. G01M 3/24 340/605 |
| 4,924,976 A | | 5/1990 | Bernett |

(Continued)

FOREIGN PATENT DOCUMENTS

| CN | 1853098 | 10/2006 |
| EP | 0140174 A1 | 5/1985 |

(Continued)

OTHER PUBLICATIONS

Notification of Transmittal of the International Search Report and the Written Opinion of the International Searching Authority from PCT/US2015/041087, dated Mar. 22, 2016.

(Continued)

*Primary Examiner* — Manish S Shah
*Assistant Examiner* — Suman K Nath
(74) *Attorney, Agent, or Firm* — Westman, Champlin & Koehler P.A.

(57) ABSTRACT

An acoustic measurement system for an industrial process asset includes a process measurement device providing a value representative of an acoustic signal near the industrial process asset based in part on a signal from an acoustic sensor positioned near the industrial process asset. A second acoustic sensor provides an acoustic value and a noise reduction component uses the acoustic value from the second acoustic sensor to affect the value provided by the process measurement device so that the value provided by the process measurement device is more representative of an acoustic signal generated by the industrial process asset.

27 Claims, 15 Drawing Sheets

(51) Int. Cl.
*G01N 29/14* (2006.01)
*G05B 23/02* (2006.01)
*G10K 11/16* (2006.01)
*G01N 29/32* (2006.01)
*G01N 29/44* (2006.01)

(52) U.S. Cl.
CPC ..... *G01N 29/4427* (2013.01); *G05B 23/0221* (2013.01); *G10K 11/161* (2013.01); *G10K 11/178* (2013.01); *G10K 11/17821* (2018.01); *G10K 11/17861* (2018.01); *G01N 2291/015* (2013.01); *G10K 2210/112* (2013.01); *G10K 2210/30231* (2013.01); *G10K 2210/507* (2013.01)

(58) Field of Classification Search
CPC ..... G01M 3/24; G01M 3/243; F16L 55/0336; F16L 55/02; F16L 55/033; F16L 55/0335; G10K 11/16; G10K 11/1786; G10K 11/161; G10K 11/002; G05B 23/0221
USPC ..... 73/592, 593, 599, 587, 40.5 A, 645, 646
See application file for complete search history.

(56) References Cited

U.S. PATENT DOCUMENTS

| | | | |
|---|---|---|---|
| 5,058,419 | A | 10/1991 | Nordstrom et al. |
| 5,515,733 | A * | 5/1996 | Lynnworth ............. G01F 1/662 73/644 |
| 5,675,506 | A * | 10/1997 | Savic ................. F17D 5/06 702/51 |
| 5,778,081 | A * | 7/1998 | Patrick ................ G10K 11/161 381/71.5 |
| 6,533,065 | B2 | 3/2003 | Zanker |
| 6,725,705 | B1 * | 4/2004 | Huebler ............... G01M 3/243 702/51 |
| 7,203,322 | B1 | 4/2007 | Bostock |
| 7,290,450 | B2 | 11/2007 | Brown et al. |
| 7,542,860 | B2 * | 6/2009 | Bechtold ............... G01H 1/00 702/189 |
| 7,624,650 | B2 | 12/2009 | Gysling et al. |
| 7,624,651 | B2 | 12/2009 | Fernald et al. |
| 7,963,177 | B2 | 6/2011 | Gysling |
| 7,975,559 | B2 | 7/2011 | Gysling |
| 8,806,947 | B2 | 8/2014 | Kajitani |
| 9,568,390 | B2 * | 2/2017 | Schoonover ......... G01M 3/007 |
| 2003/0085071 | A1 * | 5/2003 | Boast .................... F01N 1/003 181/249 |
| 2004/0123666 | A1 | 7/2004 | Ao et al. |
| 2004/0170287 | A1 | 9/2004 | Biwa et al. |
| 2008/0098818 | A1 | 5/2008 | Fernald et al. |
| 2009/0266359 | A1 | 10/2009 | Flint |
| 2011/0161037 | A1 * | 6/2011 | Sutherland ............. F16L 55/48 702/103 |
| 2012/0007743 | A1 * | 1/2012 | Solomon ............... G01M 3/243 340/605 |

FOREIGN PATENT DOCUMENTS

| | | |
|---|---|---|
| GB | 2 459 351 | 10/2009 |
| JP | 02-161393 | 6/1990 |
| JP | 6-167982 | 6/1994 |
| JP | 8-136409 | 5/1996 |
| JP | 08-307501 | 11/1996 |
| JP | 9-113350 | 5/1997 |
| JP | 10-026613 | 1/1998 |
| JP | 2004-177359 | 6/2004 |
| JP | 2007-531868 | 11/2007 |
| JP | 2010-169430 | 8/2010 |
| RU | 2241174 | 11/2004 |
| RU | 2481525 | 5/2013 |
| SU | 1651016 | 5/1991 |
| WO | WO 2014/051036 | 4/2014 |

OTHER PUBLICATIONS

Grimley, Terrence A., "Clamp-On Ultrasonic Meters as Diagnostic Tools", Jul. 2010, vol. 237, No. 7, San Antonio, TX.
Warner, Kevin et al., "Noise Reduction in Ultrasonic Gas Flow Measurement", Jun. 27-30, 1999, 4th International Symposium on Fluid Flow Measurement, Denver, CO.
The Invitation to Pay Additional Fees and Annex (Communication Relating to the Results of the Partial International Search) transmitted on Nov. 11, 2015 for corresponding PCT Application No. PCT/US2015/041087 filed on Jul. 20, 2015, 6 pages.
Office Action from Russian Patent Application 2017113833 dated Nov. 23, 2017.
Office Action from Chinese Patent Application No. 201510141453.0, dated Jul. 3, 2018.
Office Action from Canadian Patent Application 2,961,736, dated Jan. 11, 2018.
Office Action from Japanese Patent Application No. 2017-516158, dated Apr. 10, 2018.
Office Action from Canadian Patent Application No. 2,961,736, dated Oct. 2, 2018.
Office Action from Japanese Application No. 2017-516158, dated Jan. 8, 2019.

* cited by examiner

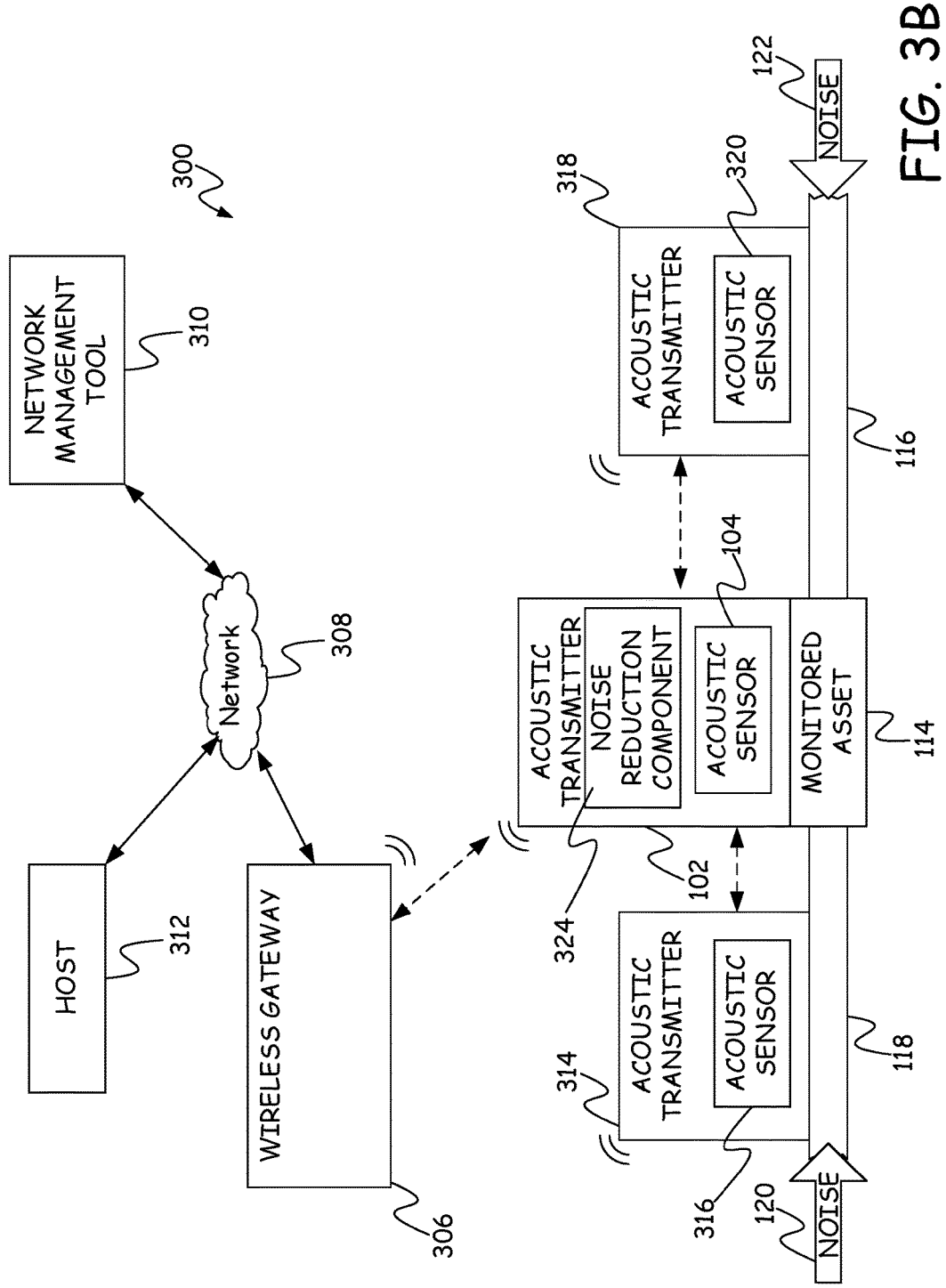

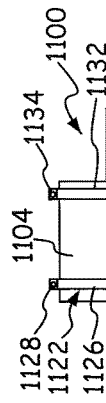
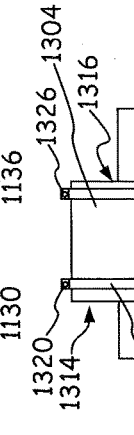
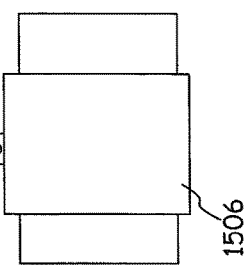

ACOUSTIC DETECTION IN PROCESS ENVIRONMENTS

BACKGROUND

Embodiments described below are related to process control. In particular, the embodiments are related to acoustic measurements in industrial plants.

In industrial process control environments, fluids and materials are processed using process equipment such as reactors, distillers, mixers, and heaters, for example. Within the industrial process control environment, the fluids and materials are housed in one or more tanks and are transported between various pieces of process equipment through conduits or piping. The movement of the fluids and materials through the conduits and tanks is controlled by one or more pumps and one or more valves including relief valves that open to relieve excess pressure. The components in a process control environment such as the process equipment, tanks, conduits, pumps and valves, for example, can be referred to generically as process elements or process assets.

Performance of the process steps is monitored by measuring one or more process variables using process transmitters that are attached to or fluidly coupled to one or more process assets. Each process transmitter contains a sensor that senses a state of a fluid or material within one or more process assets and circuitry that converts the sensor signal into one or process variables.

One example of a process transmitter is an acoustic process transmitter that measures acoustic signals associated with a process asset. For example, an acoustic process transmitter can be used to measure acoustic signals associated with a relief valve, safety valve, or steam trap to determine if the valve or trap is open or leaking. The acoustic transmitter measures the magnitude of the acoustic signal near the monitored asset and transmits a process variable representing the magnitude of the acoustic signal to a host through a network. Either the host or the acoustic process transmitter can compare the magnitude of the acoustic signal to an alarm level and trigger an alarm if the acoustic signal exceeds the threshold set for the monitored asset. Some devices also measure a temperature.

The discussion above is merely provided for general background information and is not intended to be used as an aid in determining the scope of the claimed subject matter. The claimed subject matter is not limited to implementations that solve any or all disadvantages noted in the background.

SUMMARY

An acoustic measurement system for an industrial process asset includes a process measurement device providing a value representative of an acoustic signal near the industrial process asset based in part on a signal from an acoustic sensor positioned near the industrial process asset. A second acoustic sensor provides an acoustic value and a noise reduction component uses the acoustic value from the second acoustic sensor to affect the value provided by the process measurement device so that the value provided by the process measurement device is more representative of an acoustic signal generated by the industrial process asset.

In a further embodiment, a noise level on a process structure is measured and an acoustic level near a process asset is measured. The measured acoustic level is modified based on the measured noise level to produce an adjusted acoustic level.

In a further embodiment, an acoustic measurement system includes an acoustic sensor configured to be mounted near a process pipe and an acoustic suppression device. The acoustic suppression device has at least one inner surface shaped to fit the process pipe and at least one connector for securing the acoustic suppression device to the process pipe.

In a still further embodiment, a modular noise suppression kit includes a first fin, a second fin and a plurality of spacers having different lengths. Spacers of different lengths are associated with different noise frequencies. The noise suppression kit further includes at least one connector for connecting one of the plurality of spacers between the first fin and the second fin.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 3B is a block diagram of an acoustic monitoring systems of a second embodiment.

FIG. 11 is a side sectional view of one embodiment of a noise suppression device.

FIG. 12 is a side view of the noise suppression device of FIG. 11.

FIG. 13 is a side sectional view of a second embodiment of a noise suppression device.

FIG. 14 is a side view of the noise suppression device of FIG. 13.

FIG. 15 is a side sectional view of a third noise suppression device.

FIG. 16 is a side view of the noise suppression device of FIG. 15.

DETAILED DESCRIPTION OF ILLUSTRATIVE EMBODIMENTS

Figure 1:
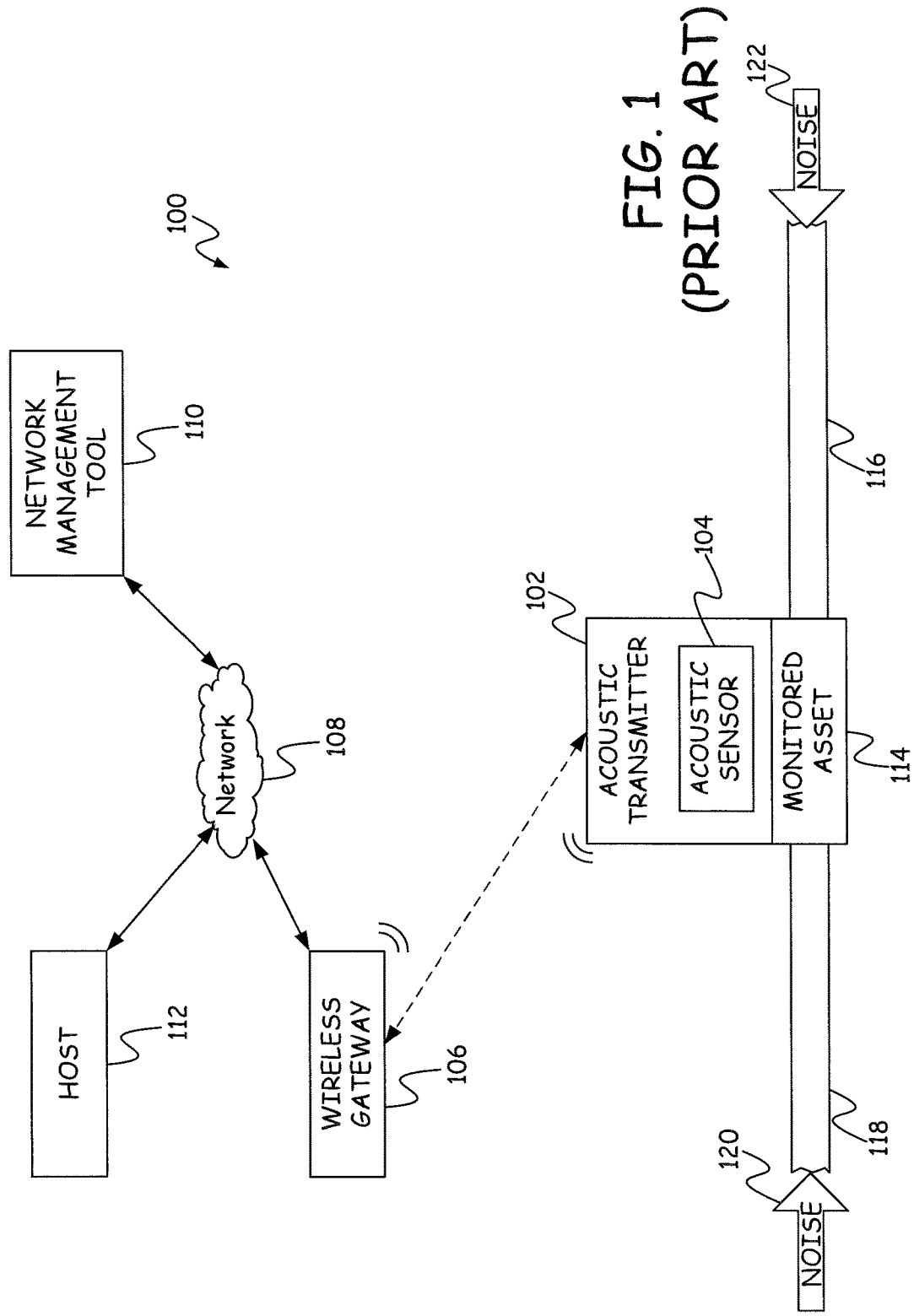
FIG. 1 is a block diagram of a prior art acoustic monitoring system.

As shown in the block diagram of FIG. 1, under the prior art, an acoustic measurement system 100 included a wireless acoustic transmitter 102, a wireless gateway 106, a network 108, a network management tool 110 and a host 112.

Wireless acoustic transmitter 102 is mounted near or on a monitored asset and includes an acoustic sensor 104 that measures an acoustic level near monitored asset 114. The acoustic level sensed by acoustic sensor 104 is converted into a digital value, if necessary, by a processor in acoustic transmitter 102 and the digital value representing the acoustic level is wirelessly transmitted by acoustic transmitter 102 to wireless gateway 106. In accordance with one embodiment, acoustic transmitter 102 and wireless gateway 106 communicate using the WirelessHart® communication protocol in accordance with IEC 62591. However, other wireless protocols may also be employed.

Wireless gateway 106 acts as an interface between wireless acoustic transmitter 102 and a wired network 108 and also acts to define and maintain a network of transmitters that are in wireless communication with gateway 106. For example, wireless gateway 106 can create and maintain a mesh network of wireless transmitters. Wireless gateway 106 receives the wireless signal from wireless acoustic transmitter 102 and conveys the acoustic level in the wireless signal to one or both of network management tool 110 and host 112 through network 108.

In alternative embodiments, acoustic transmitter 102 is a wired transmitter that is connected to host 112 through a process control loop that uses a protocol such as the HART® communication protocol in which digital information is modulated on to a 4-20 mA current, the Foundation Fieldbus communication protocol or the Profibus communication protocol, for example.

Network management tool 110 provides user interfaces and applications for monitoring networks maintained by various wireless and wired gateways. Through network management tool 110, it is possible to see what networks are available and what devices are in each network. It is also possible to see state information about various devices in each network including state information about wireless acoustic transmitter 102. In one embodiment, network management tool 110 includes an application that provides a user interface indicating the state of monitored asset 114 based on the acoustic level provided by acoustic transmitter 102.

Host 112 also provides applications for monitoring the state of devices connected to network 108 and any networks maintained by gateways attached to network 108. In accordance with one embodiment, host 112 includes an application that generates a user interface that displays the state of monitored asset 114 based on the acoustic level provided by acoustic transmitter 102.

Under the prior art, any of acoustic transmitter 102, network management tool 110 and host 112 can include an alarm function that triggers an alarm when the acoustic level detected by acoustic sensor 104 exceeds an alarm threshold.

Ideally, acoustic sensor 104 only measures the acoustic noise generated by monitored asset 114. However, as depicted in FIG. 1, noise 120 and 122 is present on process structures 118 and 116 that support or are physically connected to monitored asset 114. In a process environment, acoustic noise can travel long distances through pipes and tanks depending on the magnitude of the noise source and the transport media. It can be difficult for the low power acoustic transmitter 102 to discriminate between acoustic energy emanating from monitored asset 114 and background noise 120 and 122, generated elsewhere in the system.

Figure 2:
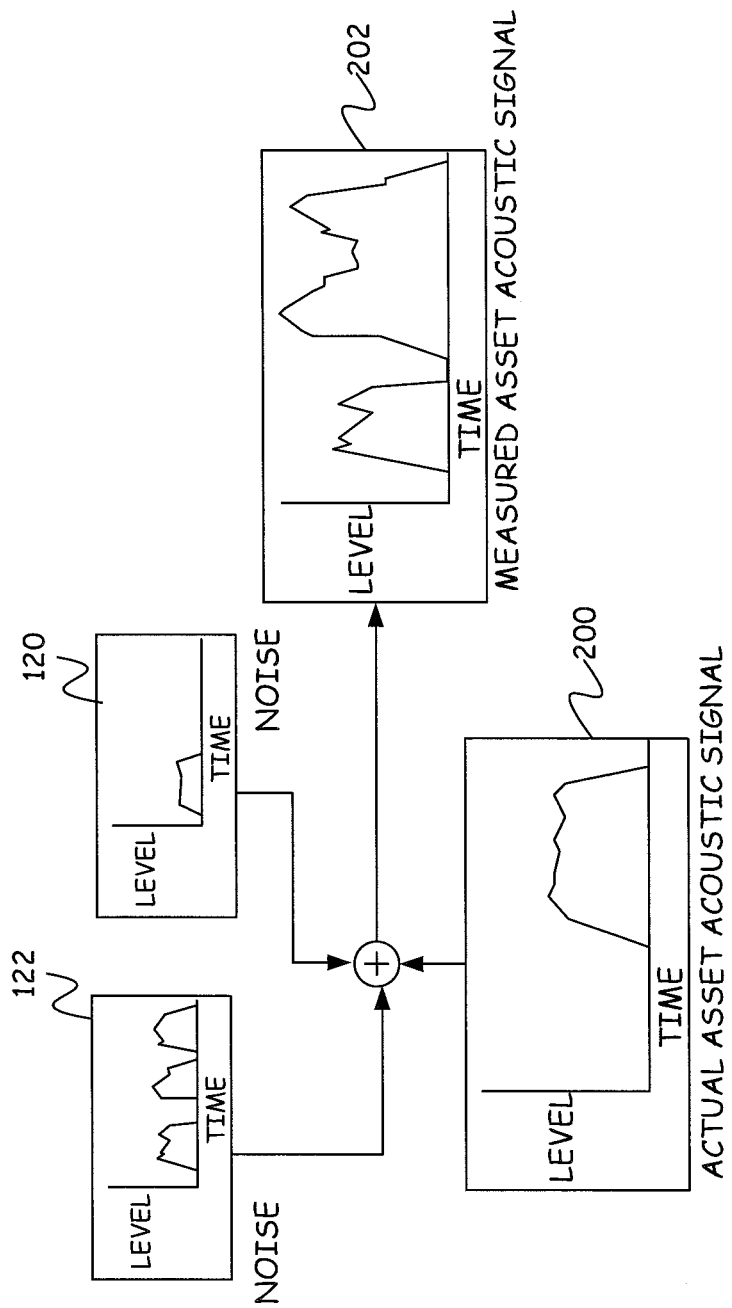
FIG. 2 is a depiction of the components of a measured asset acoustic signal under the prior art.

As a result, and as depicted in FIG. 2, noise, such as noise 120 and noise 122, is added to the actual asset acoustic signal 200 to form a measured asset acoustic signal 202, which is what is sensed by acoustic sensor 104 under the prior art. As can be seen in FIG. 2, the measured asset acoustic signal 202 can be quite different from the actual asset acoustic signal 200. At times, noise 120 and noise 122 can be so loud that it can cause the measured asset acoustic signal to cross the alarm threshold thereby triggering an alarm even though monitored asset 114 is not producing enough sound to warrant an alarm. In addition to loudness, the noise may have in-phase frequency content that combines with the measured actual asset acoustic signal. Even if the noise level is low it can combine with the asset acoustic signal if the noise frequency is in phase with the asset acoustic signal thereby increasing the amplitude sufficiently to trigger the alarm. This may occur with some applications of the device.

Figure 3A:
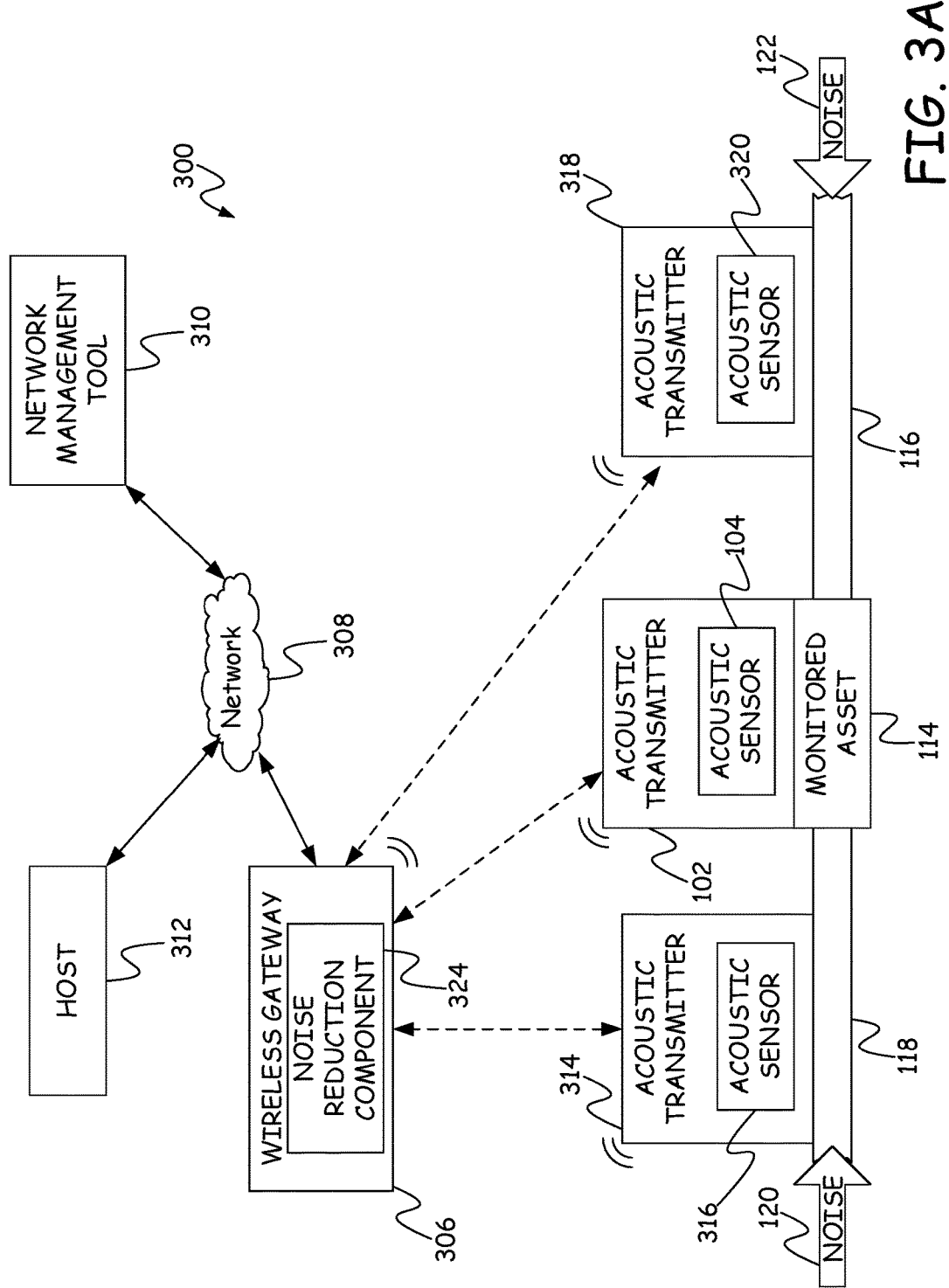
FIG. 3A is a block diagram of an acoustic monitoring system of one embodiment.

FIG. 3A provides a block diagram of an embodiment of an acoustic measurement system 300. Although FIG. 3A illustrates a wireless configuration, the present invention is also applicable to wired acoustic transmitters. In such a configuration, the various communication links illustrated between components may be wired communication links. For example, a two-wire process control loop may be used in which both power and information is conveyed over the same two wires. For example, a 4-20 mA current loop may be used in which an analog current level is used to represent a process variable. In another example embodiment, digital information is modulated onto the loop current to convey additional information. Such an embodiment may be implemented using the HART® Communication Protocol. However, other wired communication protocols may also be implemented including Profibus, Foundation Fieldbus, or others. In acoustic measurement system 300, according to one embodiment of the invention, two additional wireless acoustic transmitters 314 and 318 are provided that together with wireless acoustic transmitter 102 form a wireless network that is maintained by wireless gateway 306. Wireless acoustic transmitters 314 and 318 include two additional acoustic sensors 316 and 320, respectively. Acoustic sensor 316 senses an acoustic signal on process structure 118 while acoustic sensor 320 senses an acoustic signal on process structure 116. Thus, acoustic sensor 316 is able to measure noise 120 while acoustic sensor 320 is able to measure noise 122. Acoustic sensor 104 generates an acoustic value for the sound detected near monitored asset 114, which includes sound produced by monitored asset 114 and attenuated versions of noises 120 and 122. The acoustic values produced by acoustic sensors 316, 104 and 320 are converted into digital values and are wirelessly transmitted by their respective acoustic transmitters 314, 102 and 318 to wireless gateway 306. It is appreciated that the number of additional acoustic transmitters can vary based on the particular structure or application.

In the embodiment shown in FIG. 3A, wireless gateway 306 includes a noise reduction component 324, which reduces the noise in the acoustic values of acoustic sensor 104 based on the acoustic values of acoustic sensors 316 and 320, as described further below. The resulting filtered asset acoustic values are provided by wireless gateway 306 to one or both of network management tool 310 and host 312 through network 308.

Figure 4:
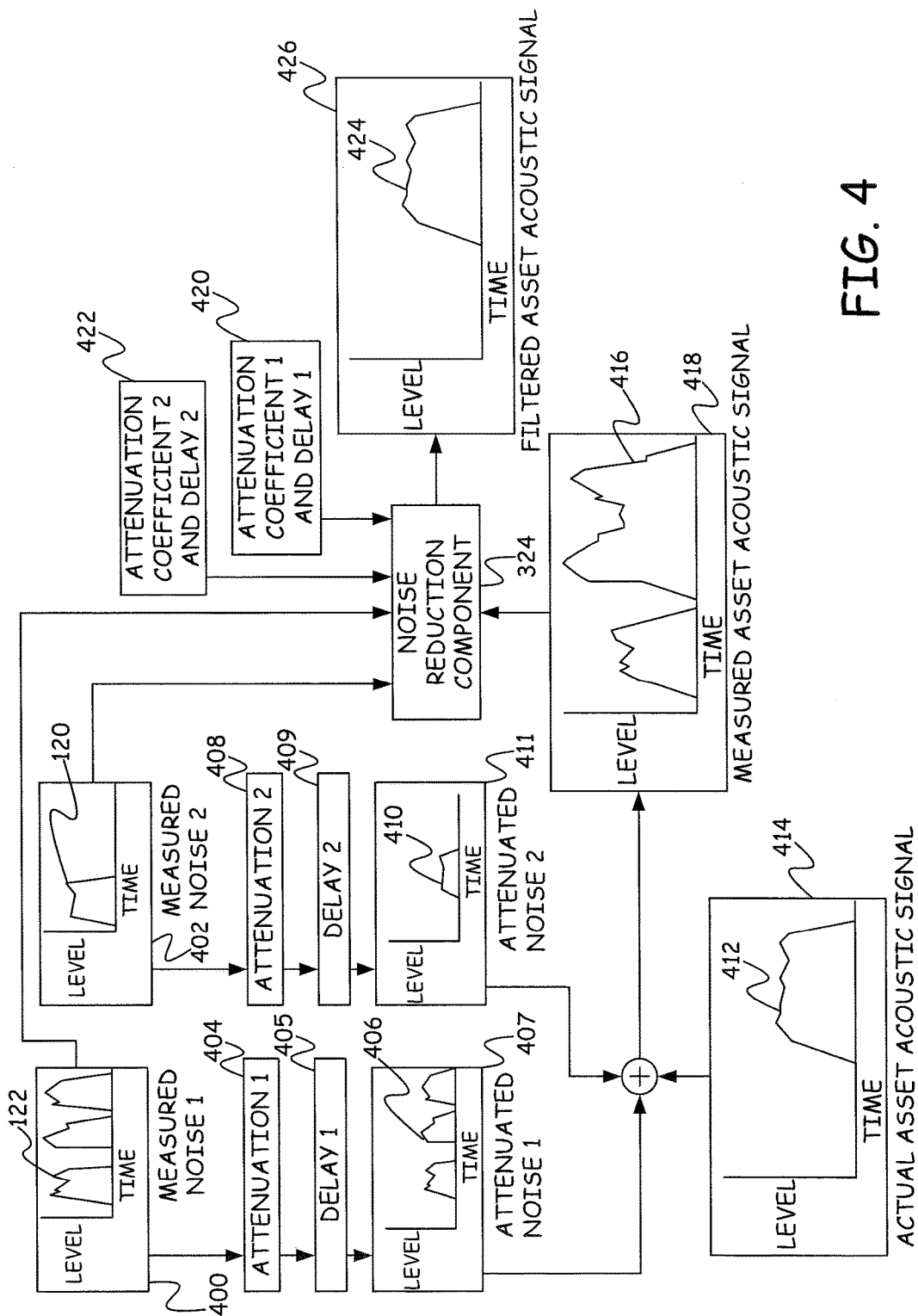
FIG. 4 depicts the formation of a filtered asset acoustic signal in accordance with one embodiment.

FIG. 4 provides a depiction of the operation of the block diagram of FIG. 3A. In FIG. 4, graphs 400 and 402 provide an example of the acoustic values generated by acoustic sensors 316 and 320, respectively, over time. In graphs 400 and 402, the vertical axis shows the magnitude of the acoustic signal as measured by the respective acoustic sensor and the horizontal axis shows time. Thus, graph 400 shows the magnitudes of noise 122 at sensor 320 and graph 402 shows the magnitudes of noise 120 at sensor 316.

As noise 122 progresses along structure 116 from acoustic sensor 320 to monitored asset 114, it experiences an attenuation 404. In addition, since it takes a period of time for noise 122 to propagate along structure 116, noise 122 experiences a propagation delay 405. As a result of the attenuation and delay, at monitored asset 114, noise 122 has become attenuated and delayed noise 406 as depicted in graph 407. As shown in graph 407, attenuated and delayed noise 406 is smaller in magnitude than noise 122 and is shifted later in time. Similarly, as noise 120 propagates along process structure 118, it is attenuated by an attenuation 408 and delayed by a propagation delay 409 to produce an attenuated and delayed noise 410 as shown in graph 411. Attenuated and delayed noise 406 and attenuated and delayed noise 410 combined with actual asset acoustic signal 412 shown in graph 414. This combined signal is what acoustic sensor 104 senses resulting in measured asset acoustic signal 416 as shown in graph 418.

In this embodiment, measured noise 120, which is the acoustic signal generated by acoustic sensor 316, measured noise 122, which is the acoustic signal generated by acoustic sensor 320 and measured asset acoustic signal 416, which is the acoustic value generated by acoustic sensor 104, are all provided to noise reduction component 324. In addition, noise reduction component 324 receives a first attenuation coefficient and delay 420 and a second attenuation coefficient and delay 422. Attenuation coefficient and delay 420 represents attenuation 404 and delay 405 and attenuation coefficient and delay 422 represents attenuation 408 and delay 409. Using attenuation coefficient and delay 420, noise reduction component 324 reduces measured noise 122 and delays measured noise 122 to produce an attenuated and delayed noise that approximates attenuated and delayed noise 406. Similarly, noise reduction component 324 uses attenuation coefficient and delay 422 to reduce measured noise 120 and delay measured noise 120 to produce an attenuated and delayed noise that approximates attenuated and delayed noise 410. Noise reduction component 324 then subtracts the approximations to attenuated and delayed noises 406 and 410 from measured asset acoustic signal 416. The result of this subtraction is filtered asset acoustic signal 424 as shown in graph 426.

As shown in graph 426, filtered asset acoustic signal 424 is a more accurate representation of actual asset acoustic signal 412. As a results, noise reduction component 324 reduces the number of false alarms generated based on the signal from acoustic sensor 104.

In FIG. 3A, each of acoustic transmitters 314, 318 and 102 communicate with wireless gateway 306 and the noise reduction component is present in wireless gateway 306. In such an embodiment, wireless gateway 306 acts as a process control device that provides a value representative of an acoustic signal near industrial process asset 114 based in part on a signal from acoustic sensor 104 positioned near industrial process asset 114 and noise reduction component 324 uses the acoustic values from acoustic sensors 316 and 320 to affect the acoustic value provided by wireless gateway 306 such that the value provided by wireless gateway 306 is more representative of the acoustic signal generated by monitored asset 104.

In other embodiments, such as shown in FIG. 3B, acoustic transmitters 314 and 318 communicate with acoustic transmitter 102 and provide the acoustic sensor signals produced by acoustic sensors 316 and 320 to acoustic transmitter 102 directly and acoustic transmitter 102 can include noise reduction component 324. In such an embodiment, acoustic transmitter 102 acts as a process control device that provides a value representative of an acoustic signal near industrial process asset 114 based in part on a signal from acoustic sensor 104 positioned near industrial process asset 114 and noise reduction component 324 uses the acoustic values from acoustic sensors 316 and 320 to affect the acoustic value provided by acoustic transmitter 102 such that the value provided by acoustic transmitter 102 is more representative of the acoustic signal generated by monitored asset 104. In such embodiments, acoustic transmitter 102 may be a wired transmitter instead of a wireless transmitter and may communicate the value indicative of the acoustic signal near industrial process asset 114 over a control loop to host 312 using a wired protocol such as the HART®, Foundation Fieldbus or Profibus, for example. In other embodiments where the sensor signals from acoustic sensors 316 and 320 are provided to acoustic transmitter 102, noise reduction component 324 can be present in wireless gateway 306. Acoustic transmitters 314 and 318 may communicate with acoustic transmitter 102 either wirelessly or through a direct wired connection (not shown).

In still further embodiments, noise reduction component 324 of FIG. 3A can be shifted from wireless gateway 306 to one of network management tool 310 and host 312. In such embodiments, wireless gateway 306 relays the acoustic values from acoustic transmitters 102, 314 and 318 to the network management tool 310 or host 312 that contains noise reduction component 324. Regardless of where noise component 324 resides, it produces a filtered asset acoustic signal 424 that is a more accurate portrayal of the actual asset acoustic signal 412 generated by monitored asset 114. In such embodiment, the process control device, either network management tool 310 or host 312, that contains noise reduction component 324 acts as a process control device that provides a value representative of an acoustic signal near industrial process asset 114 based in part on a signal from acoustic sensor 104 positioned near industrial process asset 114 and noise reduction component 324 uses the acoustic values from acoustic sensors 316 and 320 to affect the acoustic value provided by network management tool 310 or host 312 such that the value provided by network management tool 310 or host 312 is more representative of the acoustic signal generated by monitored asset 104.

Figure 5:
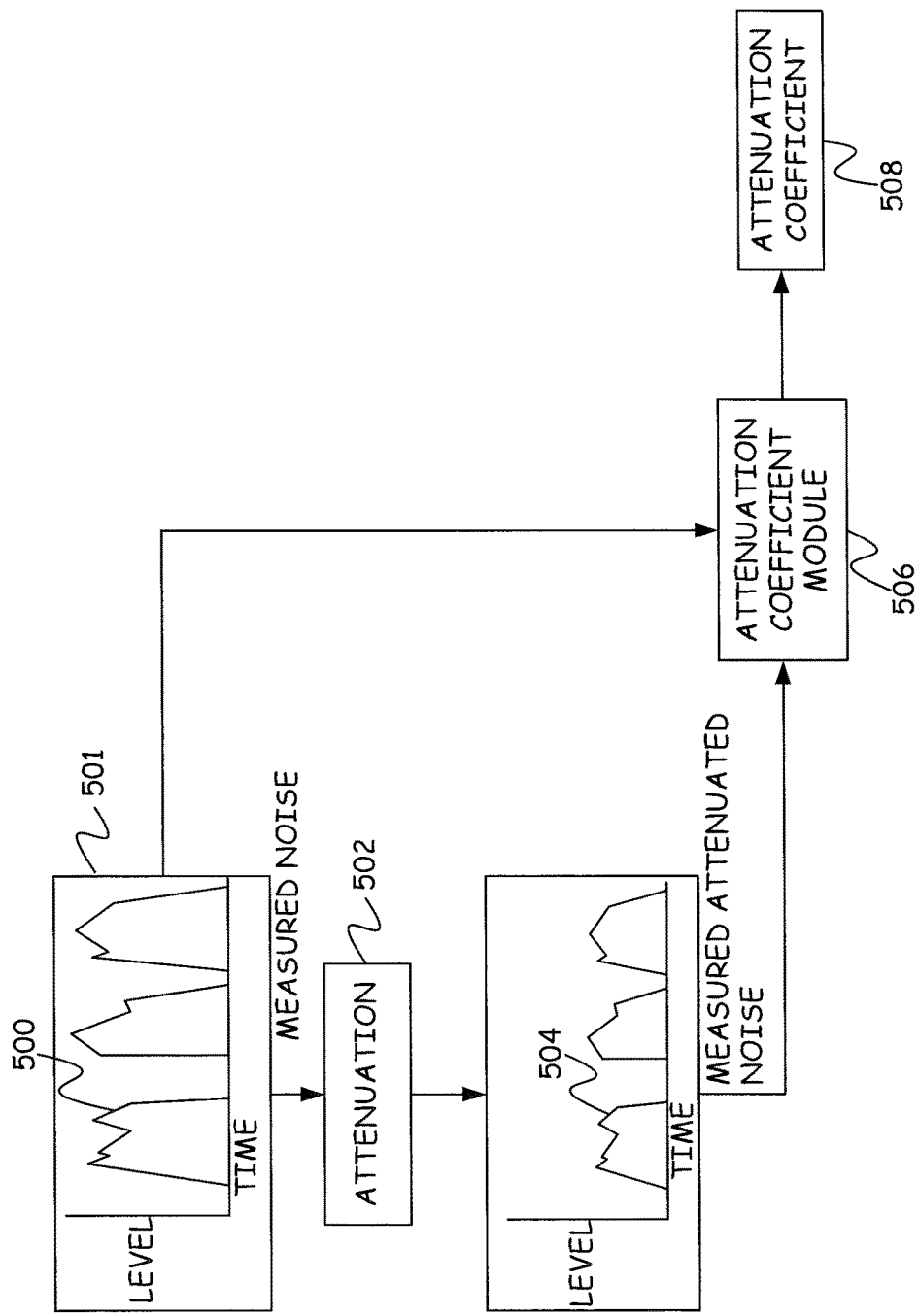
FIG. 5 depicts the formation of an attenuation coefficient in one embodiment.

FIG. 5 provides a depiction of a method for forming attenuation coefficients 420 and 422 of FIG. 4. The process of FIG. 5 is performed separately for each of acoustic sensors 316 and 320 to separately form attenuation coefficients 422 and 420. In the discussion below, the steps will be discussed while referring to acoustic sensor 320, process structure 116 and attenuation coefficient 420. However, those skilled in the art will recognize that the same steps are to be repeated for acoustic sensor 316 and process structure 118 to form attenuation coefficient 422.

Before beginning the process of FIG. 5, steps are taken to ensure that monitored asset 114 is not generating an acoustic signal. Noise emanating from the measured asset may be eliminated by ensuring that the asset is in its idle state. This can be accomplished, for example, through the closing of an isolation valve that prevents the operation of and/or leakage through the measured asset. Ideally, the steps should keep monitored asset 114 and process structures 116 and 118 in a state that is as close as possible to the expected operational state of monitored asset 114 and process structures 116 and 118. In particular, monitored asset 114 and process structures 116 and 118 should be filled with the same type of fluid expected to be carried by these elements during operation. In addition, the internal pressure and temperature within these elements should be as close as possible to the expected temperature and pressure during operation and the external environment temperature and pressure should be as close as possible to the expected external temperature and pressure during operation. Further, the velocity of the fluid or material passing through these elements should be as close as possible to the expected velocity of the fluid or material during operation.

A test noise signal or background noise is then introduced into process structure 116 and is measured by acoustic sensor 320 to provide measured noise 500 (also referred to as a measured background noise or a measured test noise) as depicted in graph 501. Ideally, measured noise 500 is as similar as possible to the noise 122 expected to be present during operation of the process environment. The noise measured at acoustic sensor 320 propagates through process structure 116 and is attenuated by an attenuation 502 to produce an attenuated noise at monitored asset 114 that is sensed by acoustic sensor 104 as measured attenuated noise 504. Measured noise 500 from acoustic sensor 320 and measured attenuated noise 504 measured by acoustic sensor 104 are provided to an attenuation coefficient module 506, which uses the values to form an attenuation coefficient 508. In accordance with one embodiment, attenuation coefficient module 506 forms attenuation coefficient 508 by averaging measured noise 500 and measured attenuated noise 504 over some time range and then determining the ratio of the average measured attenuated noise over the average measured noise to form the attenuation coefficient.

The delay between when noise detected by acoustic sensor 320 is detected by acoustic sensor 104 may be determined by introducing an impulse noise into the system and measuring the length of time between when acoustic sensor 320 detects the impulse noise and when acoustic sensor 104 detects the impulse noise. Similarly, the delay between when noise detected by acoustic sensor 316 is detected by acoustic sensor 104 may be determined by introducing an impulse noise into the system and measuring the length of time between when acoustic sensor 316 detects the impulse noise and when acoustic sensor 104 detects the impulse noise.

Figure 6:
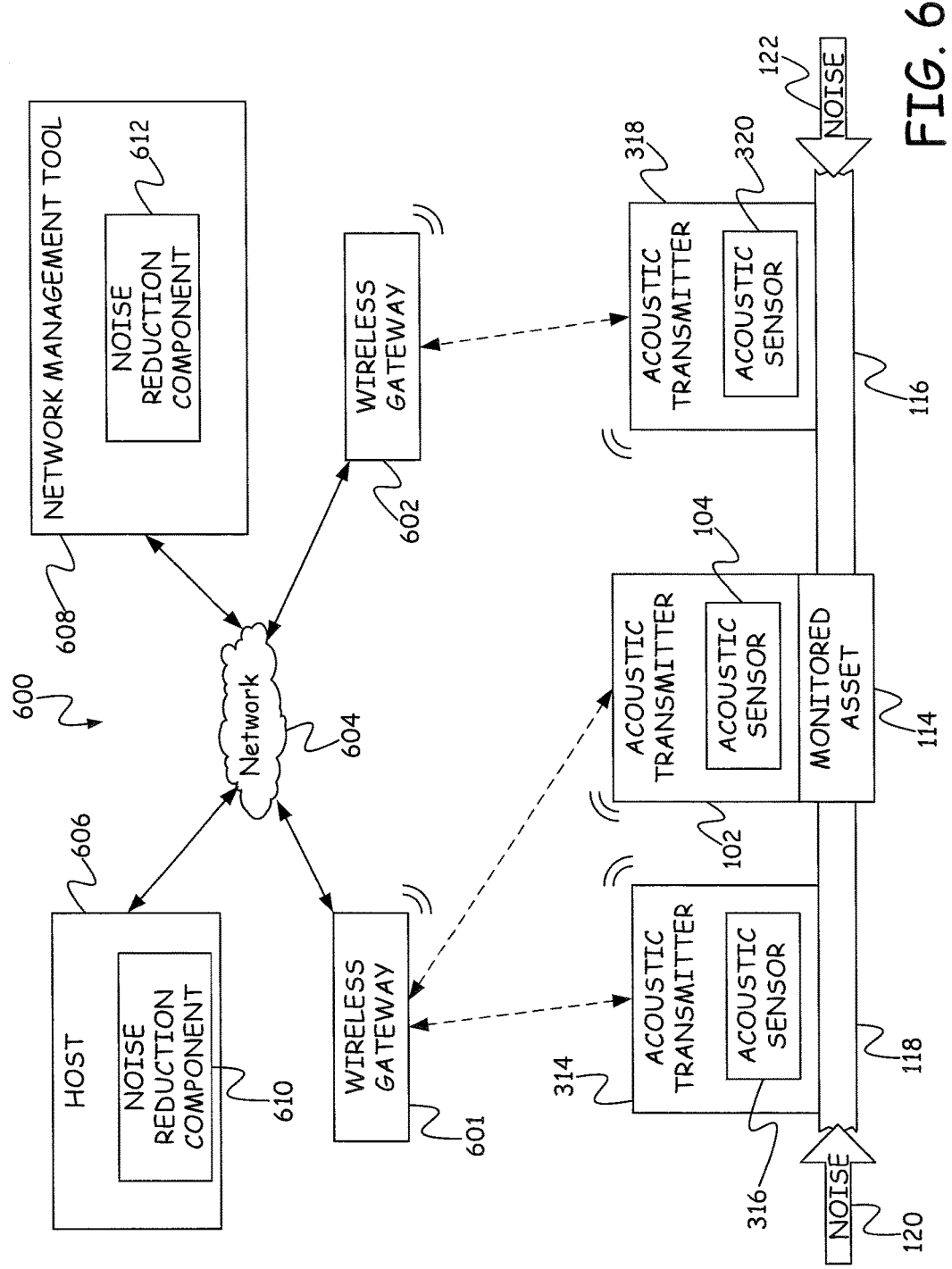
FIG. 6 is a block diagram of a second embodiment of an acoustic measurement system.

FIG. 6 provides a second embodiment of an acoustic measurement system 600 for an industrial process asset. In FIG. 6, elements that are common to FIG. 3A are similarly numbered and operate in a similar fashion as described above except for acoustic transmitter 318, which is in wireless communication with a wireless gateway 602 while acoustic transmitters 102 and 314 are in wireless communication with a separate wireless gateway 601. Thus, acoustic transmitter 318 transmits the acoustic value generated by acoustic sensor 322 to wireless gateway 602 while acoustic transmitter 102 transmits the acoustic signal generated by acoustic sensor 104 to wireless gateway 601 and acoustic transmitter 314 transmits the acoustic sensor signal generated by acoustic sensor 316 to wireless gateway 601.

Network management tool 608 provides various user interfaces to associate acoustic transmitter 318 with acoustic transmitters 102 and 314 even though acoustic transmitter 318 communicates through a separate wireless gateway. In addition, network management tool 608 can receive the acoustic sensor signals provided by acoustic transmitters 314, 102 and 318 through wireless gateways 601 and 602 and network 604. In alternative embodiments, acoustic transmitters 314, 318 and 102 are wired transmitters that communicate with network management tool 608 over a process loop using a communication protocol such as HART®, Foundation Fieldbus, or Profibus, for example, and wireless gateways 601 and 602 are not present. In accordance with one embodiment, network management tool 608 includes noise reduction components 612, which operates in an identical fashion to noise reduction component 324 of FIG. 3A. Noise reduction components 612 of network management tool 608 provides a filtered asset acoustic signal 424 that network management tool 608 can use or that network management tool 608 can forward to host 606 through network 604. In such an embodiment, network management tool 608 acts as a process control device that provides a value representative of an acoustic signal near industrial process asset 114 based in part on a signal from acoustic sensor 104 positioned near industrial process asset 114 and noise reduction component 612 uses the acoustic values from acoustic sensors 316 and 320 to affect the acoustic value provided by network management tool 608 such that the value provided by network management tool 608 is more representative of the acoustic signal generated by monitored asset 104.

Similarly, host 606 can receive acoustic sensor signals generated by acoustic sensor 320, 316 and 104 via wireless gateways 601 and 602 and network 604 or via a wired process loop. As a result, host 606 can also include a noise reduction component 610, which operates identically to noise reduction component 324 of FIG. 3A to produce the filtered asset acoustic signal. In such an embodiment, host 606 acts as a process control device that provides a value representative of an acoustic signal near industrial process asset 114 based in part on a signal from acoustic sensor 104 positioned near industrial process asset 114 and noise reduction component 610 uses the acoustic values from acoustic sensors 316 and 320 to affect the acoustic value provided by host 606 such that the value provided by host 606 is more representative of the acoustic signal generated by monitored asset 104. Note that although two noise reduction components 610 and 612 are shown in FIG. 6, only one of the noise reduction components is necessary.

Figure 7:
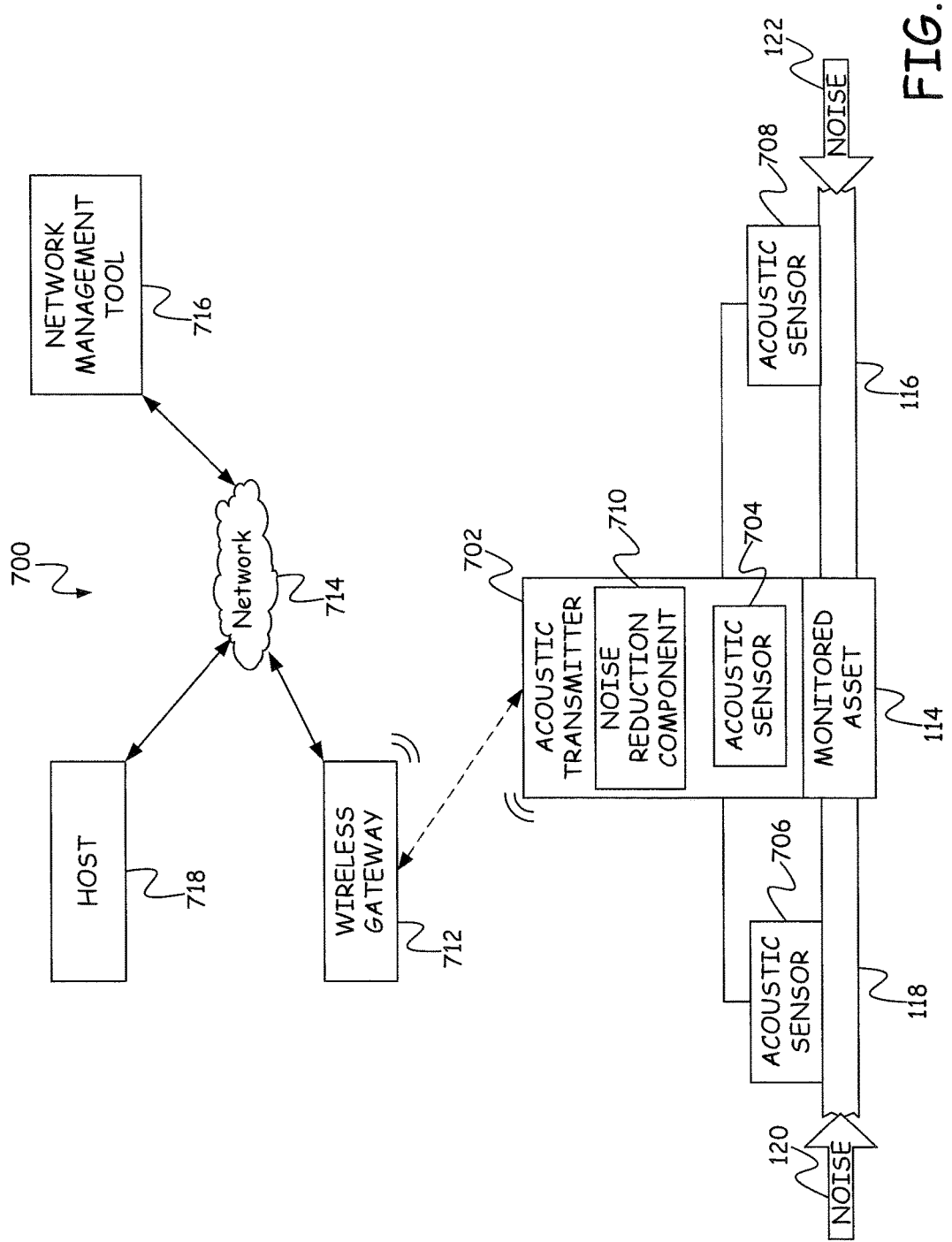
FIG. 7 is a block diagram of a third embodiment of an acoustic measurement system.

FIG. 7 provides a further embodiment of an acoustic measurement system 700 for an industrial processes asset. In the embodiment of FIG. 7, acoustic transmitters 314 and 318 of FIGS. 3A and 6 have been removed and in their place, acoustic sensors 706 and 708 are provided that are connected directly to acoustic transmitter 702. Thus, acoustic transmitter 702 receives the acoustic sensor signals of acoustic sensor 706 and acoustic sensor 708. Although acoustic sensors 706 and 708 are shown to be connected to acoustic transmitter 702 by a wired connection, in other embodiments, sensors 706 and 708 are connected by a wireless connection and include an internal power source or a separate power connection. Acoustic sensor 706 provides an acoustic signal that measures acoustic noise 120 in process equipment 118 while acoustic sensor 708 provides an acoustic sensor signal representative of acoustic noise 122 in process equipment 116. Acoustic transmitter 702 also receives an acoustic sensor signal from acoustic sensor 704 that measures the acoustic signal near monitored asset 114.

A noise reduction component 710 that operates in identical fashion to noise reduction component 324 of FIG. 3A receives the acoustic sensor signals from acoustic sensors 704, 706 and 708 and from those acoustic sensor signals produces a filtered asset acoustic signal 424 in an identical fashion to the method described in connection with FIG. 4. Acoustic transmitter 702 wirelessly transmits the filtered asset acoustic signal 424 to a wireless gateway 712, which relays the filtered asset acoustic signal to one or both of network management tool 716 and host 718 through a wired connection to a network 714. Alternatively, acoustic transmitter 702 communicates with one or both of host 718 and network management tool 716 over a wired process loop using a protocol such as HART®, Foundation Fieldbus, or Profibus, for example. In both the wireless and wired embodiments, acoustic transmitter 702 acts as a process control device that provides a value representative of an acoustic signal near industrial process asset 114 based in part on a signal from acoustic sensor 104 positioned near industrial process asset 114 and noise reduction component 710 uses the acoustic values from acoustic sensors 316 and 320 to affect the acoustic value provided by acoustic transmitter 702 such that the value provided by acoustic transmitter 702 is more representative of the acoustic signal generated by monitored asset 704.

Although noise reduction component 710 is shown to be within acoustic transmitter 702 in FIG. 7, those skilled in the art will recognize that noise reduction component 710 can be in one or more of wireless gateway 712, network management tool 716 or host 718. In embodiments where the noise reduction component 710 is not present in acoustic transmitter 702, acoustic transmitter 702 sends acoustic sensor values from acoustic sensors 704, 706 and 708 to wireless gateway 712, which either forms the filtered asset acoustic values 424 if the noise reduction component is within wireless gateway 712 or forwards the acoustic sensor values to the process device containing the noise reduction component 710, such as network management tool 716 or host 718. In other embodiments, acoustic transmitter 702 sends acoustic sensor values to one or both of network management tool 716 and host 718 over a wired process loop using a protocol such as HART®, Foundation Fieldbus, or Profibus, for example. In such embodiments, the process control device, such as wireless gateway 712, network management tool 716 or host 718, that contains noise reduction component 710 acts as a process control device that provides a value representative of an acoustic signal near industrial process asset 114 based in part on a signal from acoustic sensor 104 positioned near industrial process asset 114 and noise reduction component 710 uses the acoustic values from acoustic sensors 706 and 708 to affect the acoustic value provided by wireless gateway 712, network management tool 716 or host 718 such that the value provided by wireless gateway 712, network management tool 716 or host 718 is more representative of the acoustic signal generated by monitored asset 104.

Figure 8:
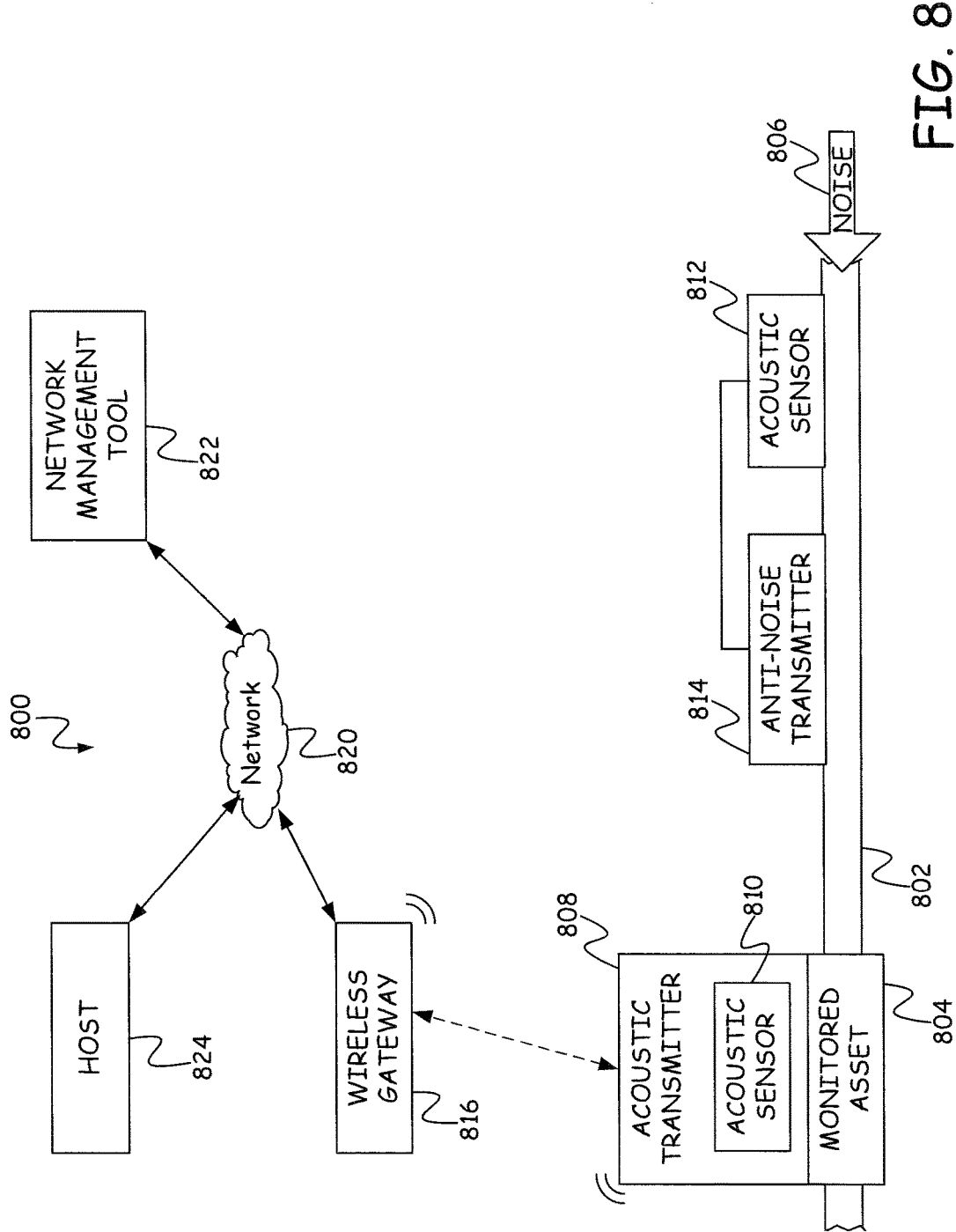
FIG. 8 is a block diagram of a fourth embodiment of an acoustic measurement system.

FIG. 8 provides a further embodiment of an acoustic measurement system 800 for an industrial process asset. In FIG. 8, a monitored process asset 804 is positioned on a process structure 802, such as conduit or piping. An acoustic transmitter 808 have an acoustic sensor 810 is positioned near monitored asset 804. Acoustic sensor 810 senses an acoustic signal and generates acoustic sensor values that are converted into digital values that are transmitted by acoustic transmitter 808 to a wireless gateway 816. Wireless gateway 816 forwards the acoustic sensor values to one or more of a network management tool 822 and a host 824 through a wired connection to a network 820. In other embodiments, acoustic transmitter 808 sends acoustic sensor values to one or both of network management tool 822 and host 824 over a wired process loop using a protocol such as HART®, Foundation Fieldbus, or Profibus, for example.

Acoustic measurement system 800 further includes an acoustic sensor 812 located on or near process structure 802 and an anti-noise transmitter 814 located on process structure 802. Acoustic sensor 812 senses a noise signal 806 on process structure 802 and transmits an acoustic value representative of acoustic noise 806 to anti-noise transmitter 814. In response to the acoustic sensor value provided by acoustic sensor 812 and an attenuation coefficient and propagation delay value, anti-noise transmitter 814 generates an acoustic signal designed to cancel acoustic noise 806. In particular, anti-noise transmitter 814 produces an acoustic signal that is a phase shifted and attenuated form of acoustic noise 806 wherein the amount of phase shifting is based on the propagation delay between acoustic sensor 812 and anti-noise transmitter 814 along process structure 802 and the amount of attenuation is based on the attenuation coefficient representing the amount of attenuation between acoustic sensor 812 and anti-noise transmitter 814. In addition, the phase shift includes a 180 degree phase shift along each frequency of acoustic noise 806 that causes the acoustic signal generated by anti-noise transmitter 814 to cancel acoustic noise 806. The phase shift may also take into account delays associated with generating the acoustic sensor signal and converting the acoustic sensor signal into the cancelling acoustic signal.

In further embodiments, anti-noise transmitter 814 may not generate an acoustic signal that completely cancels acoustic noise 806. In such embodiments, the expected residual noise that will reach monitored asset 804 can be calculated by determining a difference between acoustic noise 806 and the cancelling acoustic signal as well as the attenuation and propagation delay between anti-noise transmitter 814 and monitored asset 804. This residual noise can then be filtered from the signal detected by acoustic sensor 810 using the techniques described above for FIGS. 3-7.

By generating an acoustic signal that cancels noise 806, anti-noise transmitter 814 operates as a noise reduction component that uses the acoustic value from acoustic sensor 812 to affect the acoustic value provided by acoustic transmitter 808 such that the value provided by acoustic transmitter 808 is more representative of the acoustic signal generated by monitored asset 804. In particular, by cancelling noise 806, anti-noise transmitter 814 reduces the amount of noise reaching acoustic sensor 810 such that acoustic sensor 810 senses substantially only the sounds produced by monitored asset 804. As a result, the acoustic sensor value produced by acoustic sensor signal 810 and transmitted by acoustic transmitter 808 is more representative of the acoustic signal generated by monitored asset 804.

Figure 9:
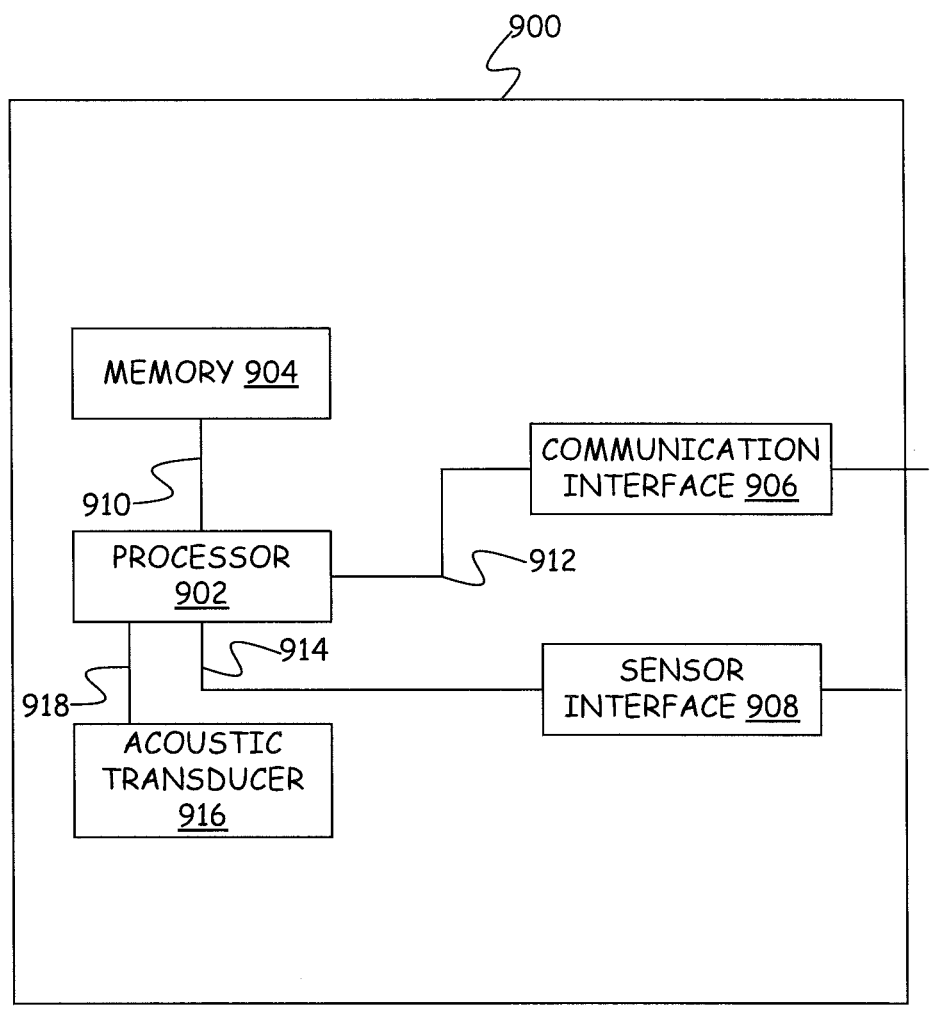
FIG. 9 is a block diagram of components of acoustic transmitters, wireless gateways, network management tools and hosts under one embodiment.

FIG. 9 provides a block diagram of elements found in a process control device 900 which is a generic representation of process control devices such as acoustic transmitters 102, 314, 318, 702 and 808; anti-noise transmitter 814, wireless gateways 106, 306, 601, 602, 712 and 816; network management tools 110, 310, 608, 716 and 822; and hosts 112, 312, 606, 718 and 824. In FIG. 9, process control device 900 includes a processor 902, a memory 904, communication interface 906, an optional sensor interface 908 and for anti-noise transmitters an acoustic transducer 916. Processor 902 communicates with memory 904 through a memory bus 910 and communicates with communication interface 906 through a communication bus 912. If optional sensor interface 908 is provided in process control device 900, processor 902 communicates with sensor interface 908 over an interface bus 914. When process control device 900 is anti-noise transmitter 814, process control device 900 communicates with acoustic transducer 916 over a connection 918. By sending a signal to acoustic transducer 916 over connection 918, processor 902 is able to cause acoustic transducer 916 to generate the cancelling acoustic signal.

Memory 904 includes processor executable instructions, such as instructions for converting an analog sensor signal to a digital sensor signal and performing the functions of noise reduction components 324, 610, 612 and 710. When process control device 900 is anti-noise transmitter 814, memory 904 includes instructions for phase shifting an acoustic sensor signal to produce a cancelling signal.

Communication interface 906 allows process control device 900 to communicate wirelessly and/or through a wired connection with other process control devices either directly or through a network connection.

Sensor interface 908 receives a sensor signal from one or more acoustic sensors and converts the analog sensor signal into sampled digital values representing a digital signal that is provided to processor 902. Sensor interface 908 is typically not present in the wireless gateway, network management tool or host and instead is typically only present in the acoustic transmitters.

Figure 10:
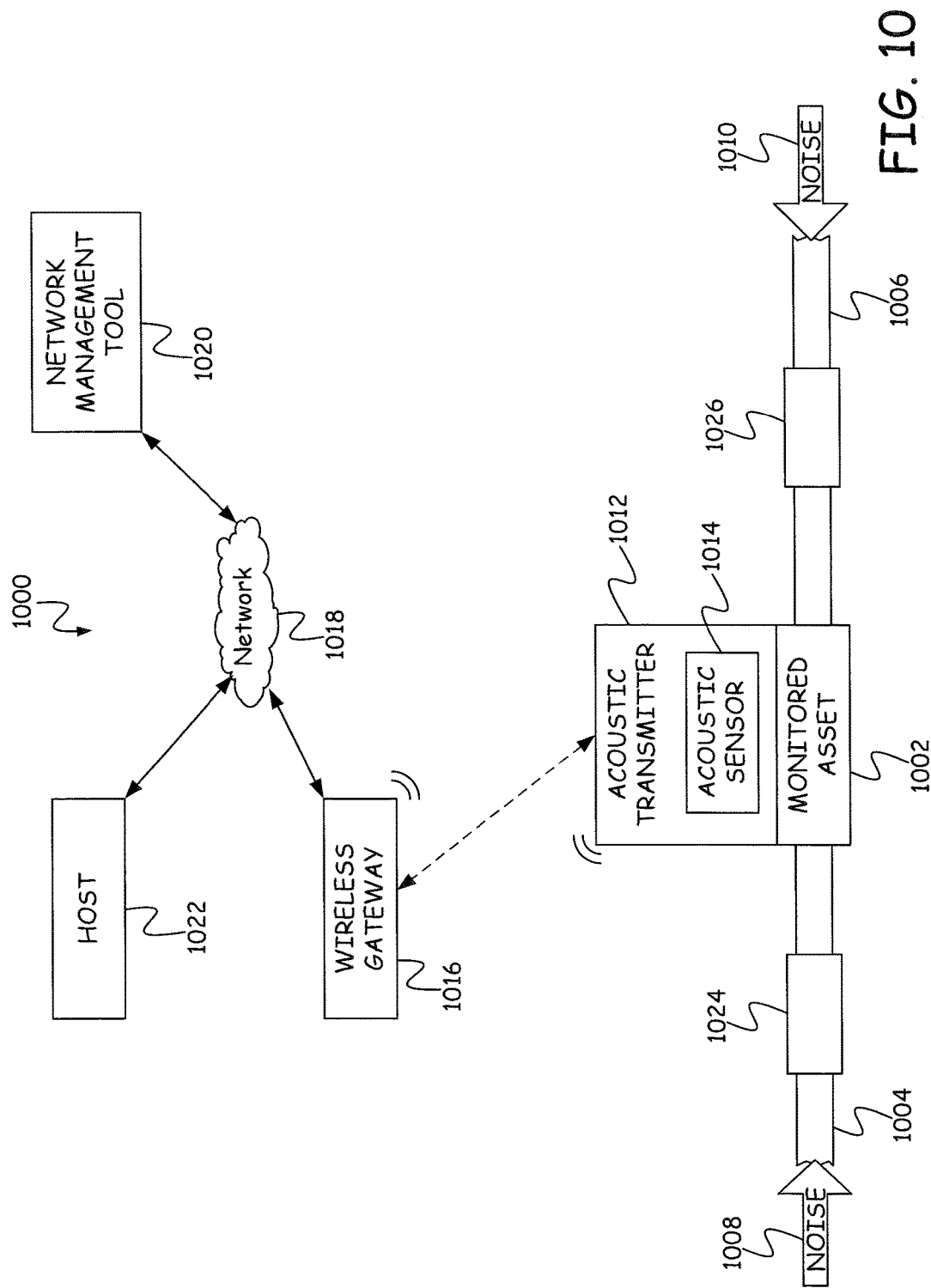
FIG. 10 is a block diagram of a fifth embodiment of an acoustic measurement system.

FIG. 10 provides a further embodiment of an acoustic measurement system 1000 for an industrial process asset. In acoustic measurement system 1000, a monitored asset 1002 is connected to process structures 1004 and 1006, which can be piping, conduits or tanks, for example. Noise 1008 is present on process structure 1004 and acoustic noise 1010 is present on process structure 1006. An acoustic transmitter 1012 is positioned near monitored asset 1002 and includes an acoustic sensor 1014 that measures an acoustic signal and provides acoustic values based on the acoustic signal. Acoustic transmitter 1012 transmits digital versions of the acoustic values to wireless gateway 1016 through a wireless connection. Wireless gateway 1016 retransmits the acoustic sensor values to one or more of a network management tool 1020 and a host 1022 through a network 1018.

Acoustic measurement system 1000 also includes acoustic suppression devices or acoustic suppressors 1024 and 1026, which are mounted on process structures 1004 and 1006, respectively. Specifically, acoustic suppressor 1024 is located between monitored asset 1002 and a noise source that generates noise 1008. Similarly, acoustic suppressor 1024 is located between monitored asset 1002 and a noise source that generates noise 1010. As a result, acoustic suppressor 1024 attenuates noise 1008 and acoustic suppressor 1026 attenuates noise 1010 such that less noise arrives at monitored asset 1002. This allows acoustic sensor 1014 to generate acoustic sensor values that are more representative of the acoustic signal generated by monitored asset 1002.

FIGS. 11 and 12 provide a sectional side view and side view, respectively, of a first embodiment 1100 of an acoustic suppressor, such as acoustic suppressor 1024 and acoustic suppressor 1026. Acoustic suppressor 1100 is positioned on a conduit 1102, which would be conduit 1004 or conduit 1006 in FIG. 10. As shown in FIG. 11, acoustic suppressor 1100 includes two sections 1104 and 1106. Section 1104 covers and is in contact with a top half of conduit 1102, while section 1106 is in contact with and covers a bottom half of conduit 1102. Sections 1104 and 1106, in one embodiment, have a generally cylindrical shape and include one or more inner cylindrical surfaces that are in direct contact with and shaped to fit the outer cylindrical surface 1108 of conduit 1102. For example, upper section 1104 includes inner cylindrical surfaces 1110, 1112 and 1114 and bottom section 1106 includes inner cylindrical surfaces 1116, 1118 and 1120. Note that in FIG. 11, not all the inner cylindrical surfaces have been referenced separately and as shown in FIG. 11, additional inner cylindrical surfaces contact outer cylindrical surface 1108 of conduit 1102.

Upper section 1104 and lower section 1106 are mounted to conduit 1102 and to each other by clamps 1122 and 1124. Clamp 1122 includes a first segment 1126, a second segment (not shown) and two connectors 1128 and 1130 that connect the segments of clamp 1122 together. Similarly, clamp 1124 includes segment 1132, a second segment (not shown) and connectors 1134 and 1136, which connect together the two segments of clamp 1124.

Although acoustic suppressor 1100 is shown to have two sections, those skilled in the art will recognize that acoustic suppressor 1100 may be divided into more than two sections such as three, four or five sections, for example, and may not extend entirely around the circumference of 1108 and may have spaces between. For some applications the acoustic suppressor may perform better if the sections have a small space between where they contact the cylindrical surface. A small spacing between may provide better contact with the cylindrical surface.

Top section 1104 includes an array of cantilevered flanges or fins 1140 that extend from a base 1138. Similarly, bottom section 1106 includes a base 1142 and an array of cantilevered flanges or fins 1144 that extend from base 1142. The array of flanges 1140 and 1144 are sized and positioned so as to be tuned so that their harmonic frequencies of vibration match the expected range of noise frequencies in conduit 1102. As discussed further below, the arrays of flanges 1140 and 1144 are designed to dampen both acoustic noise that moves conduit 1102 in an axial direction 1146 aligned with an axis 1150 of conduit 1102 as well as acoustic noise that moves conduit 1102 a direction 1148 that is transverse to axis 1150. Note that although transverse direction 1148 is shown as being in a particular direction in FIG. 11, the arrays of flanges 1140 and 1144 will suppress noise-induced radial movement of conduit 1102 in any direction that is perpendicular to axis 1150. By suppressing the noise-induced movements of conduit 1102, suppressor 1100 attenuates or suppresses the noise carried by conduit 1102.

FIGS. 13 and 14 provide a sectional side view and a side view, respectively, of a second embodiment of an acoustic suppressor 1300 mounted to a process conduit 1302. Acoustic suppressor 1300 includes a top section 1304 and a bottom section 1306 that have respective inner cylindrical surfaces 1310 and 1312 that are in direct contact with and shaped to fit an outer cylindrical surface 1308 of conduit 1302. Top section 1304 and bottom section 1306 have a generally cylindrical shape and together extend around the entire outer circumference 1308 of conduit 1302. Although acoustic suppressor 1300 is shown as only having two sections 1304 and 1306, in other embodiments, acoustic suppressor 1300 may be divided into more sections such as three, four or five sections, for example, and may not extend entirely around the circumference of 1308 and may have spaces between. For some applications the acoustic suppressor may perform better if the sections have a small space between where they contact the cylindrical surface. A small spacing between may provide better contact with the cylindrical surface.

Top sections 1304 and 1306 are mounted to conduit 1302 and bound together by clamps 1314 and 1316. Clamp 1314 includes a first segment 1318 and a second segment (not shown), which are connected together by connectors 1320 and 1322. Clamp 1316 includes a first segment 1324 and a second segment (not shown) that are connected together by connectors 1326 and 1328.

As shown in FIG. 13, lower section 1306 includes a base 1340 that forms the inner cylindrical surface 1312 and an array of cantilevered flanges 1342 that extend from base 1340. An outer casing 1344 connects to base 1340 and extends around cantilevered flanges 1342 but does not contact cantilevered flanges 1342. Similarly, top section 1304 includes a base 1346 that defines inner cylindrical surface 1310. An array of cantilevered flanges 1348 extend from base 1346 and an outer covering 1350 is connected to base 1346 and surrounds cantilevered flanges 1348 without contacting cantilevered flanges 1348. The array of cantilevered flanges 1342 and the array of cantilevered flanges 1348 are sized and spaced from each other in order to be tuned to the expected frequency ranges of noise carried by conduit 1302. In particular, the arrays of flanges are designed to harmonically oscillate at the frequencies associated with the noise carried by conduit 1302. The arrays of flanges 1342 and 1348 are designed to dampened noise-induced movement of conduit 1302 both in an axial direction 1352 that is parallel to an axis 1354 of conduit 1302 and a transverse direction 1356 that is perpendicular to axis 1354. Note that although transverse direction 1356 is shown as being in a particular direction in FIG. 13, the arrays of flanges 1342 and 1348 will suppress noise-induced radial movement of conduit 1302 in any direction that is perpendicular to axis 1354. By suppressing the noise-induced movements of conduit 1302, suppressor 1300 attenuates or suppresses the noise carried by conduit 1302.

FIGS. 15 and 16 provide a side sectional view and a side view, respectively, of an acoustic suppressor 1500 representing a third embodiment. Acoustic suppressor 1500 is mounted to a process conduit 1502 and includes an outer casing 1506, an inner dampening material 1512, a first connection bracket 1516, a second connection bracket 1518 and a connector 1520. Inner dampening material 1508 has an inner cylindrical surface 1512 that is in contact with and shaped to fit an outer cylindrical surface 1510 of conduit 1502. Outer casing 1506 and dampening material 1508 are substantially cylindrical except for a small gap at two terminating ends, one of which is shown in FIG. 15 as end 1520. The ends of outer casing 1506 and 1508 are clamped together by connector 1520 through brackets 1516 and 1518.

Together, dampening material 1508 and outer covering 1506 dampen noise-induced movement along axial direction 1550, which is parallel to an axis 1552 of conduit 1502 as well as noise-induced movement of conduit 1502 in a transverse direction 1554, which is perpendicular to axis 1552. Note that although only a single direction is shown for transverse movement 1554, acoustic suppressor 1500 will suppress noise-induced movement of conduit 1502 in any direction that is perpendicular to axis 1552. By suppressing the noise-induced movements of conduit 1502, suppressor 1500 attenuates or suppresses the noise carried by conduit 1502.

Figure 17:
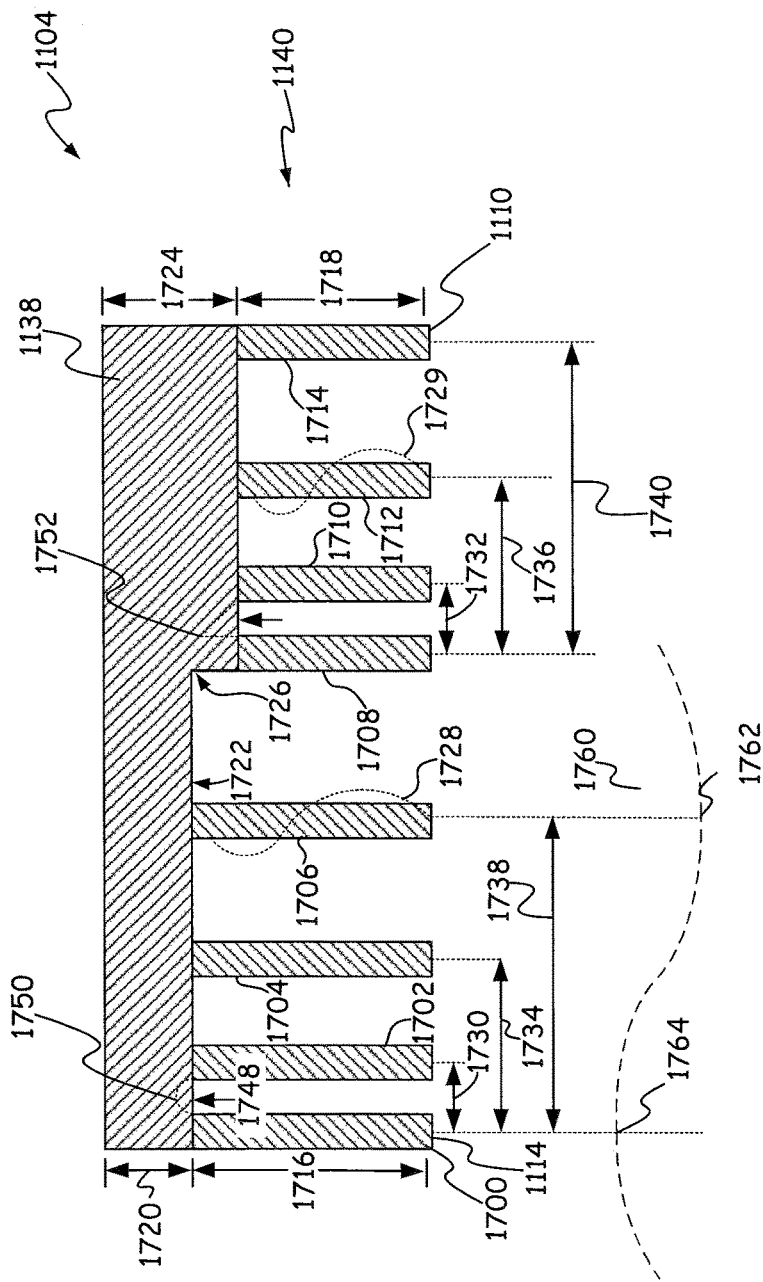
FIG. 17 is an enlarged sectional view of one embodiment of a noise suppression device.

FIG. 17 provides an enlarged sectional view of section 1104 of acoustic suppressor 1100 in accordance with one embodiment. In FIG. 17, array of flanges 1140 is shown to include flanges 1700, 1702, 1704, 1706, 1708, 1710, 1712 and 1714. Flanges 1700, 1702, 1704 and 1706 have a length 1716 while flanges 1708, 1710, 1712 and 1714 have a length 1718. Thus, within the array of flanges 1140, the lengths of the cantilevered flanges varies. Each of the flanges has an inner cylindrical surface that is configured to be in contact with the outer cylindrical surface 1108 of conduit 1102 (FIG. 11). This means that the free ends of each of the flanges, such as free ends 1114 and 1110 of flanges 1700 and 1714 must be aligned. In order to accommodate this alignment while providing different lengths 1716 and 1718 for the flanges, base 1138 has two different thicknesses 1720 and 1724 at two respective portions 1722 and 1726. Thickness 1724 of portion 1726 is thicker than thickness 1720 of portion 1722 resulting in length 1718 of flanges 1708, 1710, 1712 and 1714 being shorter than length 1716 of flanges 1700, 1702, 1704 and 1706.

Lengths 1718 and 1716 are selected so that the flanges are tuned to particular noise frequencies. In particular, length 1716 tunes flanges 1700, 1702, 1704 and 1706 to a first frequency of noise-induced movement of conduit 1102 in axial direction 1146. Length 1718 tunes flanges 1708, 1710, 1712 and 1714 to a second different frequency of noise-induced axial movement of conduit 1102. Noise-induced axial movement of conduit 1102 at the first frequency causes flanges 1700, 1702, 1704 and 1706 to harmonically oscillate as shown by wave 1728. Noise-induced axial movement of conduit 1102 at the second frequency causes flanges 1708, 1710, 1712 and 1714 to harmonically oscillate as shown by wave 1729. The harmonic oscillation of the flanges converts some of the noise energy in conduit 1102 into heat thereby reducing the noise-induced axial movement of conduit 1102. This reduction in the noise-induced axial movement of conduit 1102 is the same as reducing the noise at those frequencies carried by conduit 1102.

Flanges 1702, 1704 and 1706 are separated from flange 1700 by distances 1730, 1734 and 1738, respectively. Similarly, flanges 1710, 1712 and 1714 are separated from flange 1708 by distances 1732, 1736 and 1740, respectively. The array of flanges and distances can be adjusted or turned to reduce the expected noise. Thus, the distance or spacing between flanges in the array of flanges varies. For example, distances 1730, 1732, 1734, 1736, 1738, 1740 can be selected so that they are approximately ½, ¼, or ⅛ the wavelengths of expected noise. At these distances, the flanges suppress noise induced movement of conduit 1102 in transverse direction 1148. For example, if distance 1738 is set to ½ a wavelength of a noise induced movement 1760 of conduit 1102, then flange 1728 will be at a trough 1762 of that transverse movement when flange 1700 is at a peak 1764. The connection between flange 1700 and flange 1728 made through base 1138 will dampen this movement of flanges 1700 and 1728 thereby dampening the transverse movement of conduit 1102 and reducing the noise carried by conduit 1102.

The connections, such as connection 1748, between flanges is shown to be perpendicular to the flanges in FIG. 17. In other embodiments, other shaped connections may be used such as a rounded connection 1748 or a tapered connection 1752. Such different connection shapes can be used to reduce wave reflections in the flanges.

Figure 18:
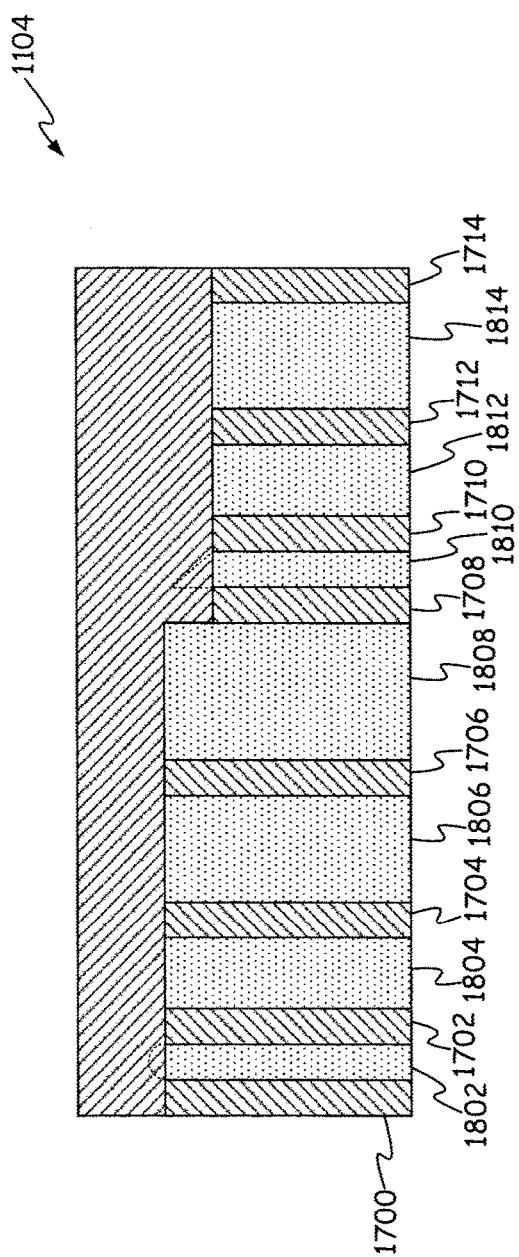
FIG. 18 is an enlarged sectional view of a second embodiment of a noise suppression device.

FIG. 18 provides a second embodiment of section 1104 of noise dampener 1100. The embodiment of FIG. 18 is identical to the embodiment of FIG. 17 with the exception of the addition of dampening materials 1802, 1804, 1806, 1808, 1810, 1812 and 1814 between flanges 1700, 1702, 1704, 1706, 1708, 1710, 1712 and 1714. Dampening materials 1802, 1804, 1806, 1808, 1810, 1812 and 1814 convert the movement of flanges 1700, 1702, 1704, 1706, 1708, 1710, 1712 and 1714 into heat and thereby further suppress noise induced movement of conduit 1102. The relative spacing and dimensions of the flanges in FIG. 18 is the same as the flanges in FIG. 17 and operate in a similar manner.

The embodiments of FIGS. 17 and 18 can also be inverted to form top part 1304 of acoustic suppressor 1300. During this inversion, the inner cylindrical surfaces of the flanges become outer cylindrical surfaces and the outer cylindrical surface of base 1138 becomes the inner cylindrical surface. Otherwise, the lengths of the flanges and the distances between the flanges remain the same.

Figure 19:
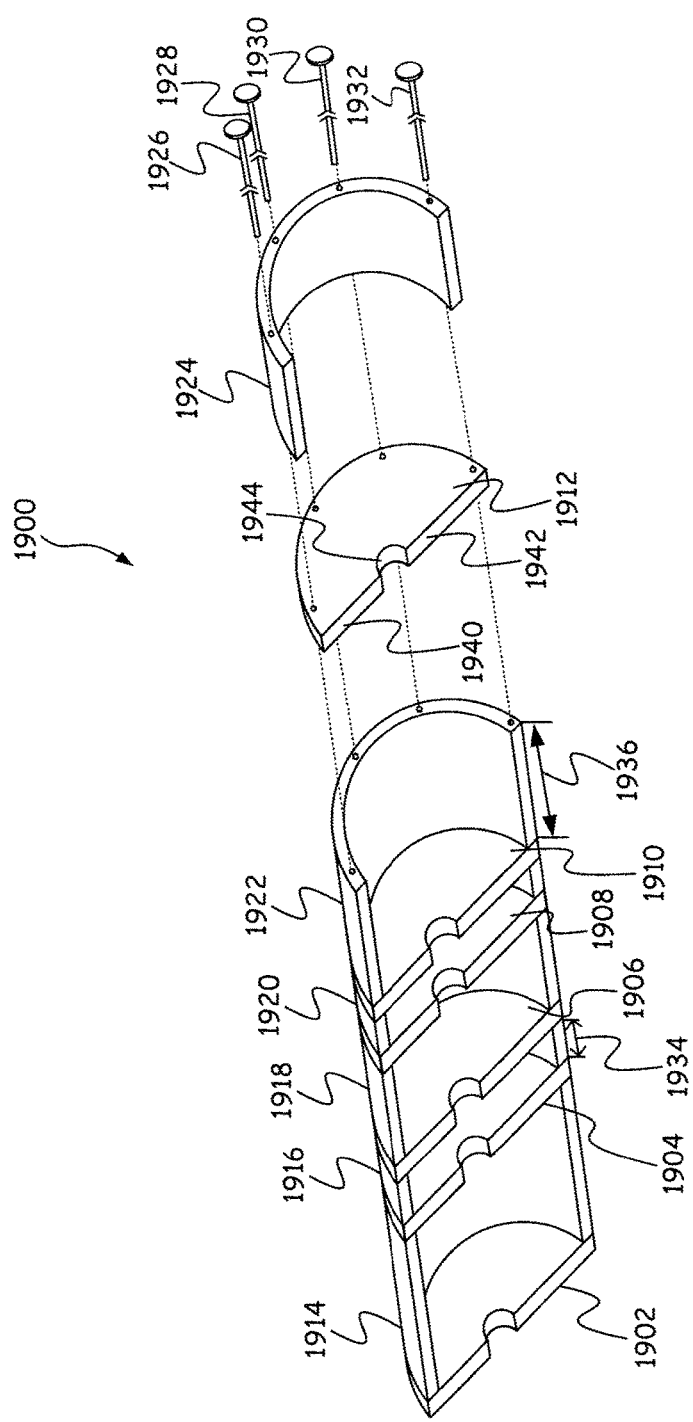
FIG. 19 provides an exploded bottom perspective view of a modular noise suppression device.

FIG. 19 provides a bottom partially exploded perspective view of a further embodiment of an acoustic suppressor 1900. Acoustic suppressor 1900 is a modular acoustic suppressor that includes modular flanges or fins 1902, 1904, 1906, 1910 and 1912 and different length modular spacers 1914, 1916, 1918, 1920, 1922 and 1924 that are connected together by connectors 1926, 1928, 1930 and 1932. The components of acoustic suppressor 1900 are part of a noise suppression kit that contains a number of different length spacers to permit the construction of an acoustic suppressor that is tuned to various frequencies of noise. For example, spacer 1916 is shown to have a length 1934 that is different from a length 1936 of spacer 1922. Since flanges are interspersed with the spacers, the lengths of the spacers determine the frequencies of noise that are suppressed by acoustic suppressor 1900. Further, since different length spacers are used in acoustic suppressor 1900, the distance between the modular flanges varies within acoustic suppressor 1900 such that multiple different frequencies of noise are dampened by acoustic suppressor 1900. As shown in FIG. 19, the spacers are partial cylinders, however in other embodiments other shapes are used for the spacers.

FIG. 19 shows only a top half of the acoustic suppressor and those skilled in the art will recognize that a bottom half identical to the top half is also provided in the kit to form a complete acoustic suppressor that surrounds a conduit. In particular, bottom surfaces of the flanges, such as bottom surface 1940 and 1942 of flange 1912 mate with top surfaces of an identical flange in the other half of the acoustic suppressor. Similarly, an inner cylindrical surfaces of the flanges, such as inner cylindrical surfaces 1944 of flange 1912 contacts an outer cylindrical surface of a conduit to transfer noise induced movement of the conduit to acoustic suppressor 1900. In further embodiments, the spacers, such as spacer 1924, include dampening material to further suppress noise induced movement of the conduit and thereby suppress noise that is carried by the conduit.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. An acoustic measurement system for an industrial process asset, the acoustic measurement system comprising:
a process control device providing a value representative of an acoustic signal at the industrial process asset based on an acoustic value from a first acoustic sensor positioned at the industrial process asset;
a second acoustic sensor mounted on a structure connected to the industrial process asset and providing an acoustic value representative of an acoustic signal at the second acoustic sensor; and
a noise reduction component that reduces a magnitude of the acoustic value from the second acoustic sensor to approximate acoustic signal attenuation along the structure between the second acoustic sensor and the first acoustic sensor, and uses the reduced magnitude to affect the value provided by the process control device so that the value provided by the process control device is representative of an acoustic signal generated by the industrial process asset.

2. The acoustic measurement system of claim 1 wherein the noise reduction component reduces a magnitude of the acoustic value from the first acoustic sensor positioned at the industrial process asset based on the reduced magnitude of the acoustic value from the second acoustic sensor.

3. The acoustic measurement system of claim 2 wherein the noise reduction component reduces the magnitude of the acoustic value from the first acoustic sensor positioned at the industrial process asset by subtracting the reduced magnitude of the acoustic value provided by the second acoustic sensor from the magnitude of the acoustic value from the first acoustic sensor.

4. The acoustic measurement system of claim 3 wherein the magnitude of the acoustic value provided by the second acoustic sensor is reduce by applying an attenuation coefficient to the acoustic value provided by the second acoustic sensor, wherein the attenuation coefficient is indicative of the acoustic signal attenuation along the structure between second acoustic sensor and the first acoustic sensor.

5. The acoustic measurement system of claim 4 wherein the attenuation coefficient is determined by receiving an acoustic test signal from the second sensor and an acoustic test signal from the first acoustic sensor positioned at the industrial process asset when the industrial process asset is not generating acoustic energy.

6. The acoustic measurement system of claim 1 wherein the noise reduction component comprises an anti-noise transmitter that generates a signal that cancels at least a portion of acoustic noise sensed by the second acoustic sensor.

7. The acoustic measurement system of claim 6 wherein the anti-noise transmitter generates the signal that cancels at least a portion of the acoustic noise based on an attenuation coefficient and a propagation delay value.

8. The acoustic measurement system of claim 1 wherein the process control device comprises an acoustic transmitter.

9. The acoustic measurement system of claim 8 wherein the second acoustic sensor and the first acoustic sensor communicate with the acoustic transmitter and the noise reduction component is within the acoustic transmitter.

10. The acoustic measurement system of claim 1 wherein the first acoustic sensor is part of a first acoustic transmitter and the second acoustic sensor is part of a second acoustic transmitter.

11. The acoustic measurement system of claim 10 wherein the second acoustic transmitter provides the acoustic value of the second acoustic sensor directly to the first acoustic transmitter and the noise reduction component is within the first acoustic transmitter.

12. The acoustic measurement system of claim 1 wherein the process control device comprises a wireless gateway and the noise reduction component is within the wireless gateway.

13. The acoustic measurement system of claim 1 wherein the process control device comprises a host and the noise reduction component is within the host.

14. The acoustic measurement system of claim 1 wherein the process control device comprises a network management tool and the noise reduction component is within the network management tool.

15. The acoustic measurement system of claim 1 further comprising:

an acoustic suppression device comprising:
- at least one inner surface shaped to fit a process pipe; and
- at least one connector for securing the acoustic suppression device to the process pipe.

16. The acoustic measurement system of claim 15 wherein the acoustic suppression device is located between a mounting location for the acoustic sensor and a noise source.

17. The acoustic measurement system of claim 15 wherein the acoustic suppression device further comprises at least two cantilevered flanges.

18. The acoustic measurement system of claim 17 wherein the at least two cantilevered flanges comprise an array of cantilevered flanges such that within the array, the spacing between the cantilevered flanges varies.

19. The acoustic measurement system of claim 17 wherein the acoustic suppression device further comprises a damping material between the at least two cantilevered flanges.

20. The acoustic measurement system of claim 17 wherein the at least two cantilevered flanges comprise an array of cantilevered flanges such that within the array, the length of the cantilevered flanges varies.

21. The acoustic measurement system of claim 20 wherein the at least two cantilevered flanges comprise an array of cantilevered flanges such that within the array, the spacing between the cantilevered flanges varies.

22. The acoustic measurement system of claim 15 wherein the acoustic suppression device further comprises modular flanges interspersed with modular spacers.

23. The acoustic measurement system of claim 22 wherein the modular spacers comprise partial cylinders.

24. The acoustic measurement system of claim 22 wherein the distance between modular flanges due to the modular spacers varies.

25. A method comprising:
- measuring a noise level at a location on a process structure;
- reducing a magnitude of the noise level to approximate noise attenuation that occurs along the process structure between the location and a process asset to form an attenuated noise level;
- measuring an acoustic level at the process asset;
- modifying the acoustic level based on the attenuated noise level to produce an adjusted acoustic level.

26. The method of claim 25 wherein reducing the magnitude of the noise level comprises applying an attenuation coefficient to the noise level to form the attenuated noise level; and wherein modifying the acoustic level comprises subtracting the attenuated noise level from the acoustic level.

27. The method of claim 26 further comprising determining the attenuation coefficient through steps comprising:
- reducing noise generated by the process asset;
- measuring an average background noise level on the process structure;
- measuring an average background noise level at the process asset;
- determining a ratio of the average background noise level at the process asset to the average background noise level on the process structure.

* * * * *